(12) United States Patent
Barcelo et al.

(10) Patent No.: US 10,935,494 B2
(45) Date of Patent: Mar. 2, 2021

(54) MATRIX WITH PLASMONICALLY ACTIVE NANO STRUCTURES

(71) Applicant: Hewlett-Packard Development Company, L.P., Houston, TX (US)

(72) Inventors: Steven Barcelo, Palo Alto, CA (US); Anita Rogacs, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 272 days.

(21) Appl. No.: 15/940,937

(22) Filed: Mar. 29, 2018

(65) Prior Publication Data
US 2019/0025218 A1   Jan. 24, 2019

Related U.S. Application Data

(63) Continuation-in-part of application No. 15/792,732, filed on Oct. 24, 2017, which is a continuation-in-part of application No. PCT/US2017/042871, filed on Jul. 19, 2017.

(51) Int. Cl.
*G01N 21/65* (2006.01)
*G01N 33/543* (2006.01)
*G01N 21/64* (2006.01)

(52) U.S. Cl.
CPC ..... *G01N 21/658* (2013.01); *G01N 33/54373* (2013.01); *G01N 21/648* (2013.01)

(58) Field of Classification Search
CPC .............. G01N 21/78; G01N 33/84; G01N 2021/7759; G01N 21/658; G01N 33/54373; G01N 21/648; B05D 1/18
See application file for complete search history.

(56) References Cited

U.S. PATENT DOCUMENTS

| | | | |
|---|---|---|---|
| 7,776,425 B2 | 8/2010 | Kalkan | |
| 7,871,570 B2 | 1/2011 | Huang et al. | |
| 8,687,186 B2 | 4/2014 | Wang | |
| 9,274,058 B2 | 3/2016 | Li et al. | |
| 9,719,926 B2 | 8/2017 | Astier et al. | |
| 2009/0140206 A1 | 6/2009 | Nie et al. | |
| 2011/0165077 A1 | 7/2011 | Qian | |
| 2013/0021605 A1 | 1/2013 | Yi et al. | |
| 2013/0107254 A1 | 5/2013 | Yu | |

(Continued)

FOREIGN PATENT DOCUMENTS

| CN | 103409734 A | 11/2013 |
|---|---|---|
| CN | 104359893 A | 2/2015 |

(Continued)

OTHER PUBLICATIONS

Yu et al.,"Inkjet Printed Surface Enhanced Raman Spectroscopy Array on Cellulose Paper" Anal. Chem. 2010, 82, 9626-9630 (Year: 2010).*

(Continued)

*Primary Examiner* — Dennis White
(74) *Attorney, Agent, or Firm* — Rathe Lindenbaum LLP

(57) ABSTRACT

A surface enhanced luminescence (SEL) sensing stage may include a matrix and plasmonically active nanostructures retained within the matrix, wherein no greater than 10% of the plasmonically active nanostructures consist of a single unagglomerated plasmonically active nano particle.

20 Claims, 10 Drawing Sheets

(56) References Cited

U.S. PATENT DOCUMENTS

| | | | |
|---|---|---|---|
| 2014/0081150 A1 | 3/2014 | Chu et al. | |
| 2014/0209837 A1* | 7/2014 | Barcelo | G01N 21/658 252/408.1 |
| 2015/0185156 A1 | 7/2015 | Mirkin et al. | |
| 2015/0253321 A1 | 9/2015 | Chou et al. | |
| 2017/0050046 A1 | 2/2017 | Walder et al. | |
| 2017/0167981 A1 | 6/2017 | Hu et al. | |

FOREIGN PATENT DOCUMENTS

| | | |
|---|---|---|
| CN | 106669872 | 5/2017 |
| KR | 20160119318 A | 10/2016 |
| WO | WO2010073260 | 7/2010 |
| WO | WO2013185167 | 12/2013 |
| WO | WO 2016195389 | 12/2016 |

OTHER PUBLICATIONS

Chang H. Lee, Plasmonic Paper as a Highly Efficient SERS Substrate, Army Research Laboratory (Sep. 2012).

Wang,Y.et al., Fabrication of Patternable Nanopillars for Microfluidic Sers Devices Based on Gap-induced Uneven Etching (Jan. 2015),http://ieeexplore.ieee.org/document/70.

Homan, Kimberly et al. "Silica-coated Gold Nanoparticles: Surface Chemistry, Properties, Benefits and Applications," (2017). Available at: https://www.sigmaaldrich.com/technical-documents/articles/materials-science/silica-coated-gold-nanoparticles.html.

Mao, Angelo S. et al. "Deterministic Encapsulation of Single Cells in Thin Tunable Microgels for Niche Modeling and Therapeutic Delivery," Nat Mater. 16, No. 2 (2017): 236-243.

Schwenke, Andreas et al. "Non-agglomerated Gold-PMMA Nanocomposites by in Situ-stabilized Laser Ablation in Liquid Monomer for Optical Applications" Applied Physics A 111, No. 2 (2013): 451-457.

* cited by examiner

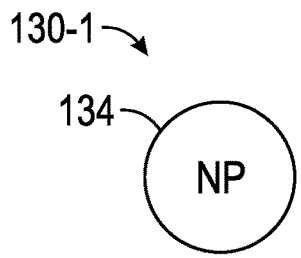

FIG. 3

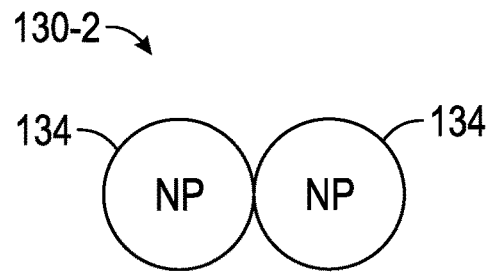

FIG. 4

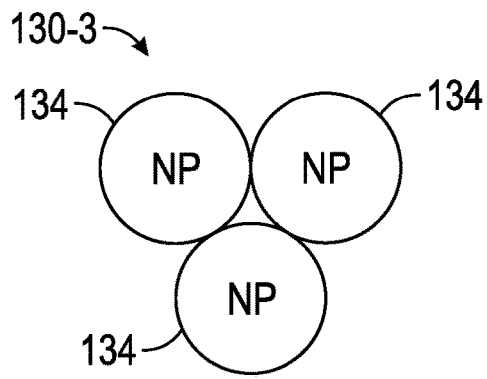

FIG. 5

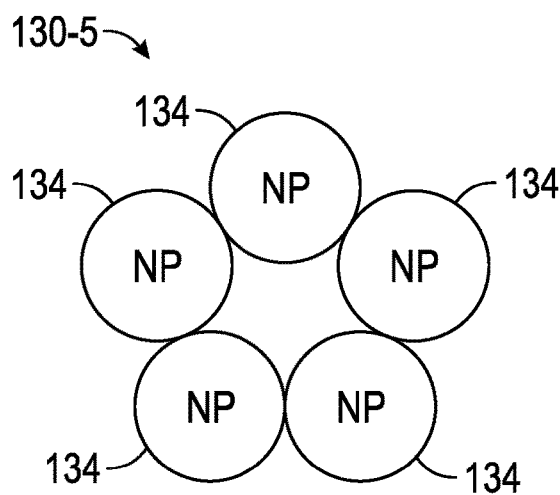

FIG. 6

```
200 ─┐
204 ─┐
┌─────────────────────────────────────────────────────────┐
│ Provide a solution having a solvent in which plasmonically active │
│ nanostructures are suspended, wherein no greater than 10% of the │
│ plasmonically active nanostructures consist of a single │
│ unagglomerated plasmonically active nano particle │
└─────────────────────────────────────────────────────────┘
206 ─┐         ↓
┌─────────────────────────────────────────────────────────┐
│ Deposit the solution with the plasmonically active nanostructures │
│ into a matrix │
└─────────────────────────────────────────────────────────┘
210 ─┐         ↓
┌─────────────────────────────────────────────────────────┐
│ Evaporate the solvent │
└─────────────────────────────────────────────────────────┘
```

FIG. 7

MATRIX WITH PLASMONICALLY ACTIVE NANO STRUCTURES

The present application is a continuation application claiming priority under 35 USC 120 from co-pending U.S. patent application Ser. No. 15/792,732 filed on Oct. 24, 2017 by Barcelo et al. and entitled MICROFLUIDIC CHIP WITH ANCHORED NANO PARTICLE ASSEMBLY which claims priority under 35 USC 119 from co-pending PCT patent application PCT/US2017/042871 filed Jul. 19, 2017 and entitled PROTECTED NANO-PARTICLE ASSEMBLIES, the full disclosures both of which are hereby incorporated by reference.

BACKGROUND

Surface enhanced luminescence (SEL) is sometimes used for analyzing the structure of inorganic materials and complex organic molecules. SEL may also be used to perform spectroscopic tagging for identifying, tracking, in vivo analysis and the like. SEL may involve the use of a stage providing plasmonically active surfaces and supporting the substance being analyzed or tested. SEL focuses electromagnetic radiation or light onto the stage supporting the substance, wherein the interaction between the light and the substance is detected for analysis. The plasmonically active surfaces of the stage may enhance such interactions to enhance performance.

BRIEF DESCRIPTION OF THE DRAWINGS

FIG. 3 is a schematic diagram of an example single nano particle nano structure.

FIG. 4 is a schematic diagram of an example dimer nano structure.

FIG. 5 is Mac diagram of an example trimer nano structure.

FIG. 6 is a schematic diagram of an example pentamer nano structure.

FIG. 7 is a flow diagram of an example method for forming an example SEL stage.

Figure 1:
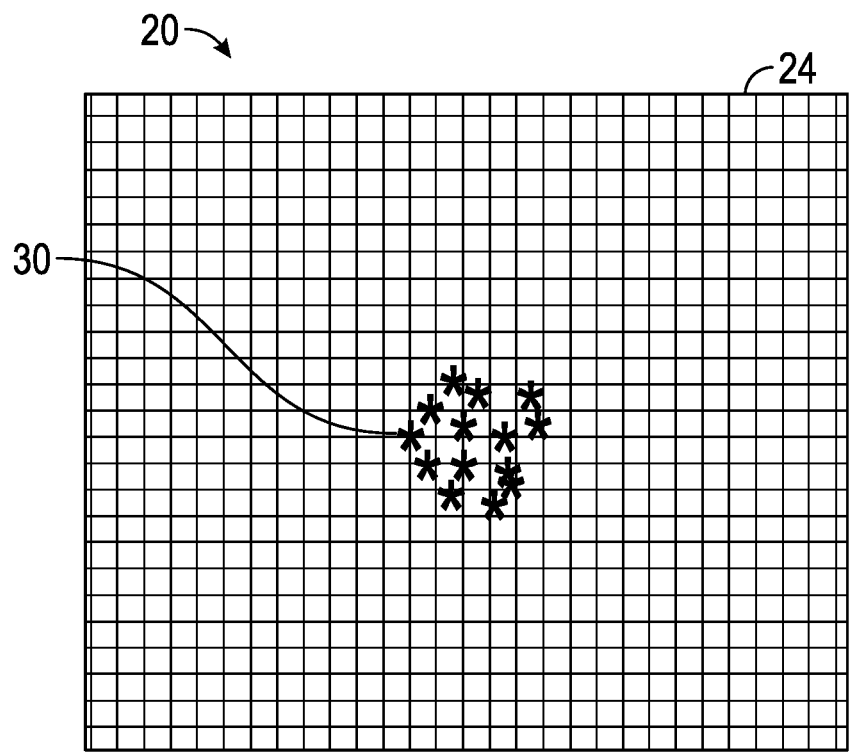
FIG. 1 is a top view schematically illustrating portions of an example SEL stage.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed herein are example SEL stages and methods that utilize or form engineered plasmonically active nanostructures retained in a matrix. The disclosed stages and method for forming such stages utilize such a matrix to provide a low cost SEL stage that is less complex, that may be more easily fabricated and that may be more easily stored or transported. In some implementations, the matrix may additionally provide filtering of nontargeted substances.

The disclosed stages and methods for forming such stages provide a controlled population of plasmonically active nanostructures. The population of the plasmonically active nanostructures may be controlled with respect to the percentage of agglomerated versus on agglomerated active nanoparticles, controlled with respect to the uniform geometry of such plasmonically active nanostructures (pentamer and the like), controlled with respect to the uniform number of nanoparticles in the plasmonically active nanostructures and/or controlled with respect to the average size of such plasmonically active nanostructures. The controlled population of plasmonically active nanostructures in the stage may lead to more consistent, repeatable, reliable and accurate SEL results.

Disclosed herein is an example surface enhanced luminescence (SEL) sensing stage may include a matrix and plasmonically active nanostructures retained within the matrix, wherein no greater than 10% of the plasmonically active nanostructures consist of a single unagglomerated plasmonically active nano particle.

Disclosed herein is an example method that may include providing a solution having a solvent in which plasmonically active nanostructures are suspended, wherein no greater than 10% of the plasmonically active nanostructures consist of a single unagglomerated plasmonically active nano particle. The method may further include depositing the solution with the plasmonically active nanostructures into a matrix and evaporating the solvent.

Disclosed herein is an example method that may include providing a solution having a solvent in which plasmonically active nanostructures are suspended, wherein at least 70% of the nanostructures in the solution have a uniform number of nanoparticles. The method may further include depositing the solution with the plasmonically active nanostructures into a matrix and evaporating the solvent.

Disclosed herein is an example method that may include providing a solution having a solvent in which plasmonically active nanostructures are suspended, wherein at least 70% of the plasmonically active nanostructures have a uniform geometry. The method may further include depositing the solution with the plasmonically active nanostructures into a matrix and evaporating the solvent.

Disclosed herein is an example method that may include providing a solution having a solvent in which plasmonically active nanostructures are suspended, wherein the plasmonically active nanostructures, excluding the nanostructures consisting of a single unagglomerated nano particle, have an average hydrodynamic radius of at least 90 nm as measured by dynamic light scattering. The method may further include depositing the solution with the plasmonically active nanostructures into a matrix and evaporating the solvent.

Disclosed herein is an example SEL applicator that may include a reservoir containing a solution of a solvent in which plasmonically active nanostructures are suspended, wherein no greater than 10% of the plasmonically active nanostructures consist of a single unagglomerated plasmonically active nano particle, a nozzle; and a fluid actuator to controllably eject the solution through the nozzle into a matrix.

FIG. 1 schematically illustrates portions of an example SEL stage 20. Stage 20 utilizes engineered plasmonically active nanostructures retained in a matrix. Stage 20 utilizes such a matrix to provide a low cost SEL stage that is less complex, that may be more easily fabricated and that may be more easily stored or transported. In some implementations, the matrix may additionally provide filtering of nontargeted substances. Stage 20 has a controlled population of plasmonically active nanostructures. The population of the plasmonically active nanostructures may be controlled with respect to the percentage of agglomerated versus unagglomerated active nanoparticles, controlled with respect to the uniform geometry of such plasmonically active nanostructures (pentamer and the like), controlled with respect to the uniform number of nanoparticles in the plasmonically active nanostructures and/or controlled with respect to the average size of such plasmonically active nanostructures. The controlled population of plasmonically active nanostructures in stage 20 may lead to more consistent, repeatable, reliable and accurate SEL results. Stage 20 comprises matrix 24 and plasmonically active nanostructures 30, each individual nano structure 30 being schematically illustrated with an "*".

Matrix 24 comprises an absorbent or porous medium having internal cells, pockets or voids sized to receive and retain plasmonically active nanostructures 30. In one implementation, matrix 24 may comprise a cellulose matrix formed from a cellulose material such as a paper or paper-like material. In another implementation, matrix 24 may comprise an open cell foam or a fabric formed from a polymer, an organic material or other materials. In other implementations, matrix 24 may comprise other lateral flow materials such as a nitrocellulose membrane polymer having an electrostatic binding mechanism, a polyvinylidene fluoride membrane polymer having a hydrophobic primary binding mechanism, a (discharge-modified) nylon membrane polymer having an (ionic) electrostatic primary binding mechanism or a polyestersulfone membrane polymer having a hydrophobic primary binding mechanism. In one implementation, matrix 24 is provided as a sheet or panel. In other implementations, matrix 24 may be provided in the form of a block or other mass of absorbent or porous material.

Figure 2:
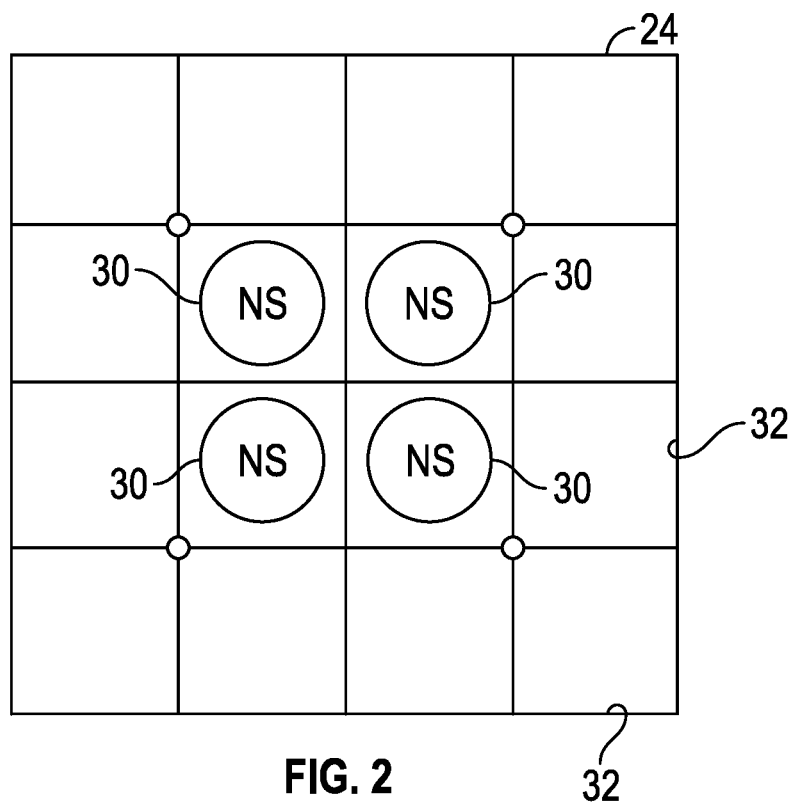
FIG. 2 in is an enlarged view of a portion of the example SEL stage of FIG. 1.

FIG. 2 is an enlarged view of a portion of stage 20, illustrating retention of some of plasmonically active nanostructures 30 by a portion of matrix 24. As schematically shown by FIG. 2, in the example illustrated, matrix 24 comprises a grid-like array of pockets, voids or cells 32. Such cells 32 are each individually sized to contain an individual nano structure 30. In other implementations, such cells 32 may be sized to contain multiple individual plasmonically active nanostructures 30. In one implementation, openings between adjacent cells 32 are sufficiently large to permit passage of plasmonically active nanostructures 30 therethrough. In some implementations, plasmonically active nanostructures 30 are retained by being absorbed onto the framework or surfaces of cells 32.

Plasmonically active nanostructures 30 comprise plasmonically active structures captured, retained and/or supported by matrix 24 within an interior of matrix 24 or along a surface of matrix 24. Each nano structure 30 comprise a plasmonically active surface, a surface that enhances plasmon resonance during SEL interrogation. FIGS. 3-6 schematically illustrate examples of different plasmonically active nanostructures. FIG. 3 illustrates an example nano structure 130-1 in the form of a single nano particle 134. Nano particle 134 may comprise an individual particle having a plasmonic surface, such as a surface formed noble metals, such as ruthenium (Ru), rhodium (Rh), palladium (Pd), silver (Ag), osmium (Os), iridium (Ir), platinum (Pt), and gold (Au), as well as copper, or alloys thereof. Other metals may be used to provide the plasmonic surfaces, such as aluminum (Al), titanium (Ti), or other metals.

FIGS. 4-6 illustrate plasmonically active nanostructures in the form of multimers, plasmonically active nanostructures formed by an agglomeration or joining of multiple nanoparticles 134. FIG. 4 illustrates nano structure 130-2, a dimer, an agglomeration of two nanoparticles 134. FIG. 5 illustrates nano structure 130-3, a trimer, an agglomeration of three nanoparticles 134. Nano structure 130-3 has a generally triangular geometry. FIG. 6 illustrates nano structure 130-5, a pentamer, an agglomeration of five nanoparticles 134. Nano structure 130-5 has a generally pentagonal geometry. Such multimers may have other geometries formed by differing numbers of individual nanoparticles that have joined to form an agglomeration of nanoparticles.

Stage 20 has a controlled population of plasmonically active nanostructures 30 to provide more consistent, repeatable, reliable and accurate SEL results. Such control over the population may be achieved through controlled agglomeration by engineering the formation of multimers. Rather than forming such plasmonically active nanostructures through the relatively random agglomeration of individual nanoparticles utilizing aggregating agents, nanoparticles 30 are formed the controlled manipulation of nano structure forming pillars. In some implementations, matrix 24 may be devoid of any aggregating agents. As a result, use of stage 20 may produce cleaner spectra for an analyte or substance of interest.

In one implementation, stage 20 has a controlled population with respect to the percentage of agglomerated versus on agglomerated active nanoparticles provided in matrix 24.

For example, in one implementation, no greater than 10% of the plasmonically active nanostructures 30 in matrix 24 consist of a single unagglomerated plasmonically active nano particle, a nano structure 130-1. In one implementation, stage 20 has a controlled population of plasmonically active nanostructures 30 with respect to a uniform number of nanoparticles forming such plasmonically active nanostructures (pentamer and the like). In one implementation, at least 70% of the plasmonically active nanostructures 30 in matrix 24 have a uniform number of nanoparticles. In other words, at least 70% of the plasmonically active nanostructures 30 in matrix 24 have a same number of nanoparticles (plural). For example, at least 70% of nano structures 30 may each have five nanoparticles. In one implementation, stage 20 has a controlled population of plasmonically active nanostructures 30 with respect to geometry of the plasmonically active nanostructures. For example, in one implementation, at least 70% of the plasmonically active nanostructures 30 have a uniform geometry, the same geometry or shape. In one implementation, stage 20 has a controlled population with respect to the average size of such nanostructures. In one implementation, the plasmonically active nanostructures 30, excluding the nanostructures 130-1 consisting of a single unagglomerated nano particle, have an average hydrodynamic radius of at least 90 nm as measured by dynamic light scattering.

FIG. 7 is a flow diagram of an example method 200 for forming an example SEL stage, such as stage 24. Method 200 forms an SEL stage that provides more consistent, repeatable, reliable and accurate SEL results. Although method 200 is described in the context of forming stage 20, it should be appreciated that method 200 may likewise be utilized to form any of the SEL stages described hereafter or similar SEL stages.

As indicated by block 204, a solution having a solvent in which plasmonically active nanostructures, such as nanostructures 30, are suspended is provided. The solution has a controlled population of nanostructures. In one implementation, no greater than 10% of the plasmonically active nanostructures consist of a single unagglomerated plasmonically active nano particle.

As indicated by block 206, the solution with the controlled population of plasmonically active nanostructures is deposited into a matrix, such as matrix 24. In one implementation, the solution formed by the solvent and the controlled population of plasmonically active nanostructures, has a composition facilitating the jetting of the solution at precisely controlled locations in a matrix. This facilitates precise control over the regions a matrix 24 containing the population of plasmonically active nanostructures.

As indicated by block 210, the solvent is evaporated, leaving the plasmonically active nanostructures retained are adhered within the matrix. In one implementation, such evaporation occurs at room temperature. In some implementation, such evaporation may be further assisted through the application of airflow or heat to the stage.

In some implementations, solution has a composition such that those volatile components of the solution that evaporate leave little if any residue in matrix. For purposes of disclosure, the term "residue" refers to those materials, other than plasmonically active nanostructures, remaining in a matrix after the solvent has been evaporated. In some implementations, the solution has a composition such that upon evaporation of the solvent, any residue left in matrix 24 omits any aggregating agents which might otherwise potentially interfere with subsequent spectroscopic or SEL sensing using stage 20.

Figure 8:
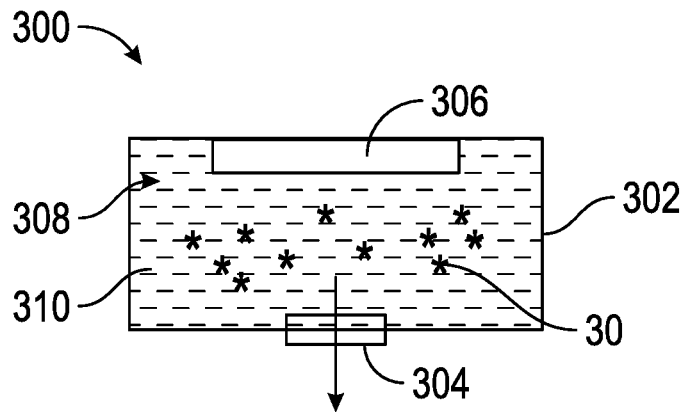
FIG. 8 is a sectional view schematically illustrating portions of an example SEL applicator.

FIG. 8 schematically illustrates portions of an example SEL applicator 300. Applicator 300 may precisely deposit a solution containing a controlled population of plasmonically active nanostructures at precise locations in a matrix, such as matrix 24 described above. Applicator 300 comprises a reservoir 302, nozzle 304 and fluid actuator 306.

Reservoir 302 comprise a chamber or volume containing a solution 308 of a solvent 310 in which plasmonically active nanostructures 30 are suspended. Each of such plasmonically active nanostructures 30 is schematically illustrated by an "*" and is described above. The solution 308 has a controlled population of such plasmonically active nanostructures 30. In the example illustrated, no greater than 10% of the plasmonically active plasmonically active nanostructures 30 consist of a single unagglomerated plasmonically active nano particle.

In other implementations, the population of solution 308 may be controlled with respect to respect a uniform number of nanoparticles forming such plasmonically active nanostructures (pentamer and the like). In one implementation, at least 70% of the plasmonically active nanostructures 30 in matrix 24 have a uniform number of nanoparticles. In other words, at least 70% of the plasmonically active nanostructures 30 in solution 308 have a same number of nanoparticles (plural). For example, at least 70% of nano structures 30 may each have five nanoparticles.

In one implementation, solution 308 has a controlled population of plasmonically active nanostructures 30 with respect to geometry of the plasmonically active nanostructures. For example, in one implementation, at least 70% of the plasmonically active nanostructures 30 in solution 308 have a uniform geometry, the same geometry or shape. In one implementation, solution 308 has a controlled population with respect to the average size of such plasmonically active nanostructures. In one implementation, the plasmonically active nanostructures 30 in solution 308, excluding the plasmonically active nanostructures 130-1 consisting of a single unagglomerated nano particle, have an average hydrodynamic radius of at least 90 nm as measured by dynamic light scattering.

Nozzle 304 comprise a constricted opening through which solution 308 may be jetted at precise locations onto a matrix. Fluid actuator 306 comprises an actuator that displaces fluid through nozzle 304 to provide such jetting. In one implementation, fluid actuator 306 may comprise a thermal resistor that, when conducting electric current, generates sufficient heat to vaporize adjacent fluid and create a bubble that drives solution 308 through nozzle 304. In other implementations, fluid actuator 306 may have other form such as a piezoelectric membrane based actuator, an electrostatic membrane actuator, a mechanical/impact driven membrane actuator, a magneto-strictive drive actuator, or other such elements that may cause displacement of fluid responsive to electrical actuation.

Figure 9:
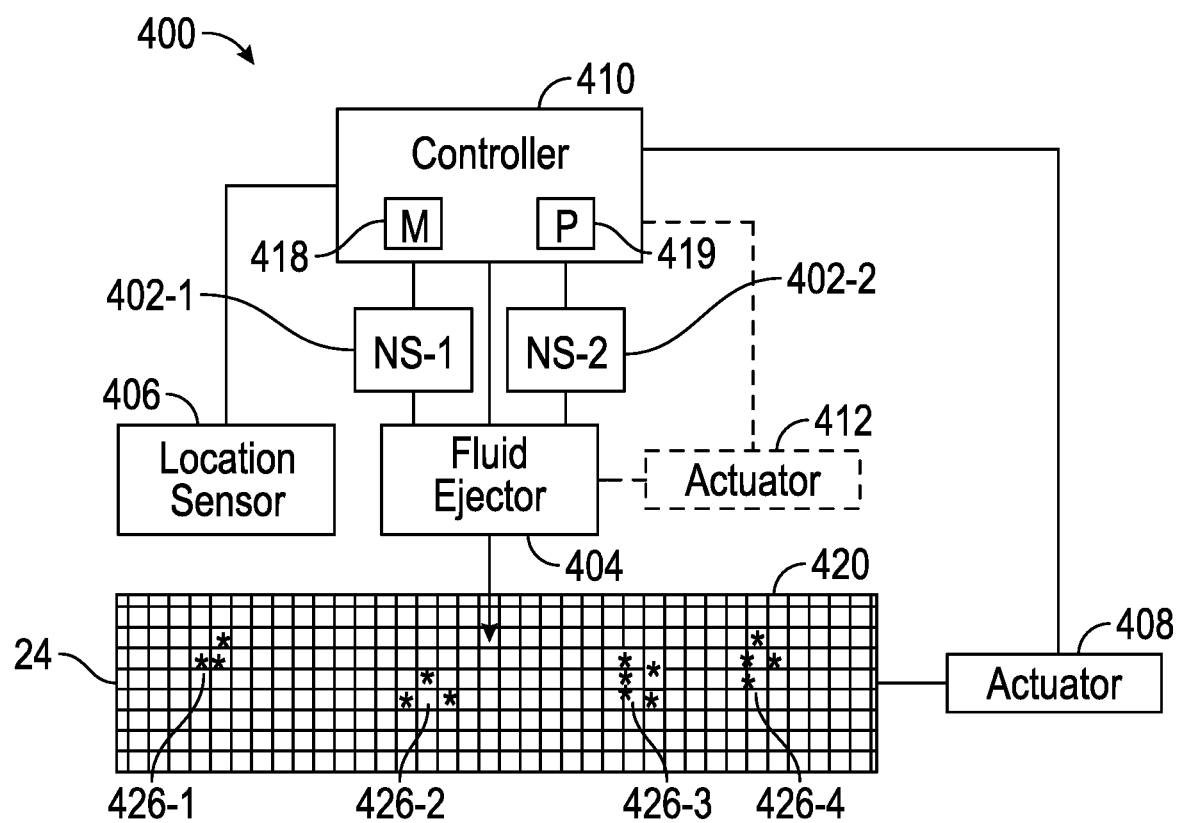
FIG. 9 is a schematic diagram of an example SEL stage forming system.

FIG. 9 schematically illustrates portions of an example SEL stage forming system 400. System 400 facilitates the formation of SEL stages having controlled populations of plasmonically active nanostructures at precise locations in different regions of the stage. In the example illustrated, system 400 for further facilitates the formation of the stage having different controlled populations of plasmonically active nanostructures at different regions of a matrix. System 400 comprises nano structure reservoirs 402-1 and 402-2

(collectively referred to as reservoirs 402), fluid ejector 404, location sensor 406, actuator 408 and controller 410.

Reservoirs 402 contain solutions formed by at least one solvent and plasmonically active nanostructures 30. In the example illustrated, each of reservoirs 402 contains a different solution. For example, reservoir 402-1 may contain a first population of plasmonically active nanostructures NS-1 while reservoir 402-2 may contain a second population of plasmonically active nanostructures NS-2 different than the first population. Although each of such populations are different, both of such populations are controlled. For example, the population of plasmonically active nanostructures in reservoir 402-1 may be controlled with respect to a first aspect (unagglomerated versus agglomerated nanoparticles, number of nanoparticles in each nano structure, geometry of the plasmonically active nanostructures or average size of the plasmonically active nanostructures) while the population of plasmonically active nanostructures in reservoir 402-1 may be controlled with respect to a second aspect different than the first aspect.

In one implementation, both of reservoirs 402 may have a population of plasmonically active nanostructures controlled with respect to the same aspect, but wherein the degree of control over the population (the percentage threshold of control) is different. For example, reservoir 402-1 may contain a first solution controlled based upon the number of nanoparticles in each nano structure, wherein at least 70% of the plasmonically active nanostructures 30 have a uniform number or the same number of nanoparticles, while reservoir 402-2 may contain a second solution also controlled based on the number of nanoparticles in each nano structure, wherein at least 90% of the plasmonically active nanostructures 30 have a uniform number or the same number of nanoparticles. Such differences between reservoirs 402 with respect to the degree of control over the population may likewise apply to agglomerated versus unagglomerated nano particle plasmonically active nanostructures, nanostructure geometry and nanostructure average size.

In one implementation, both of reservoirs 402 may have a population of plasmonically active nanostructures controlled with respect to the same aspect and having the same degree of control, but wherein the parameters or controlled values of the population are different. For example, reservoir 402-1 may contain a first solution controlled based on the number of nanoparticles in a nano structure, wherein at least 70% of the plasmonically active nanostructures 30 are formed by an agglomeration of five nanoparticles (a pentamer) while reservoir 402-2 may contain a second solution controlled based on the number of nanoparticles in a nano structure were in at least 70% of the plasmonically active nanostructures 30 are formed by an agglomeration of three nanoparticles (a trimer). Reservoir 402-1 may contain the first solution controlled such that the first solution has a first average size of plasmonically active nanostructures while reservoir 402-2 may contain a second solution controlled such that the second solution has a second average size of plasmonically active nanostructures different than the first average size. Such differences between reservoirs 402 with respect to the controlled values the population may likewise apply to nanostructure geometry and nanostructure average size.

In some implementations, the solutions in reservoirs 402 may have different populations that are differently controlled in multiple specs. The population of plasmonically active nanostructures in reservoir 402-1 may be controlled with respect to a first aspect, having a first degree of control and a first controlled the value while the population of plasmonically active nanostructures in reservoir 402-2 may be controlled with respect to a second different aspect having a second different degree of control and a second different controlled value. For example, reservoir 402-1 may have a controlled population of plasmonically active nanostructures wherein at least 70% of the plasmonically active nanostructures 30 are formed by an agglomeration of five nanoparticles while reservoir 402-1 may have a controlled population of plasmonically active nanostructures wherein at least 90% of the plasmonically active nanostructures 30 have an average radius of at least 90 nm as measured by dynamic light scattering.

Fluid ejector 404 is similar to SEL applicator 300 described above except that fluid ejector 404 selectively receives solutions from reservoirs 402 under the control of controller 410. As with applicator 300, fluid ejector 404 comprises a fluid actuator 306 which displaces fluid through a nozzle 304 (shown and described above with respect to FIG. 8) onto a matrix 24. In one such implementation, fluid ejector 404 may comprise or be connected to a valve mechanism facilitating the selective supply of fluid ejector 404 with a plasmonically active nanostructures solution from either of reservoirs 402.

Location sensor 406 comprises at least one sensing device that senses the relative location of fluid ejector 404 and matrix 24. In one implementation, location sensor 406 may comprise an optical sensor which operably detects a location marker or location indicator formed upon or carried by matrix 24. In another implementation, location sensor 406 may be carried by matrix 24, wherein locations is 406 senses positioning of fluid ejector 404. Signals transmitted from location sensor 406 to controller 410 either directly indicate the relative positioning of ejector 404 and matrix 24 or facilitate such a determination by controller 410.

Actuator 408 comprises a device operably coupled to matrix 24 to move matrix 24 relative to fluid actuator 404. In one implementation, actuator 408 comprises a conveyor. In another implementation, actuator 408 comprises a pick and place robotic device. In another implementation, actuator 408 comprises a driven spindle which unwinds matrix 24, provided as a wound web. In yet other implementations, actuator 408 may have other forms.

As shown by broken lines, in some implementations, system 400 may additionally or alternatively comprise an actuator 412. Actuator 412 is operably coupled to fluid ejector 404 so as to move or displace fluid ejector 404 relative to matrix 24. For example, in one implementation, actuator 412 may comprise a multi axis servo motor which may selectively locate fluid ejector 404 along each of the X, Y and Z axes relative to matrix 24. In other implementations, actuator 412 may have other forms.

Controller 410 comprise at least one controller that outputs control signals controlling the supply of nanostructures solution to fluid ejector 404, the relative positioning of fluid ejector 404 and matrix 24 and the time at which the fluid actuator 306 of fluid ejector 404 is actuated to control the timing at which the selected nanostructures solution is ejected and jetted onto and into matrix 24. As schematically shown by FIG. 9, controller 410 may include a non-transitory computer-readable medium 418 and a processor 419 that carries out instructions contained in the computer readable medium 418. In one implementation, the non-transitory computer readable medium 418 may be in the form of coded software programming. In one implementation, the non-transitory computer readable medium 418 may be in the form of an integrated circuit having one or more logic components.

Following instructions contained in memory 418, processor 419 outputs control signals so as to form multiple spaced regions 426-1, 426-2, 426-3 and 426-4 (collectively referred to as regions 426) in matrix 24. Each of such regions 426 is different from one another in that each of regions 426 comprises a different layout and/or different population of plasmonically active nanostructures 30 (schematically illustrated by an "*"). Although each of such regions 426 is illustrated as having a relatively small number of plasmonically active nanostructures 30, it should be appreciated that each "*" may schematically represent many plasmonically active nanostructures 30. The different layout may be different amongst regions with respect to the different patterning, surface area, surface area geometry, thickness, three-dimensional geometry/shape, volume and/or density of plasmonically active nanostructures 30 in a particular region. The different populations may be different with respect to the actual number of plasmonically active nanostructures in each region, based upon the volume or number of droplets of solution from one or both of reservoirs 402 in each region. The different populations may in addition or alternatively be different with respect to whether the plasmonically active nanostructures 30 are provided through the jetting of a solution from reservoir 402-1 or 402-2, or in situations where a particular region 426 is formed from a combination of solutions from both of reservoirs 402, the relative proportions supplied by reservoirs 402. Controller 410 may selectively actuate actuator 408 (and/or actuator 412) based upon signals from location sensor 406, may also selectively supply plasmonically active nanostructures solution from reservoirs 402 and may selectively control the time at which such solutions are ejected or jetted at particular locations of matrix 24 based upon signals from location sensor 406. In one implementation, memory 418 may contain or receive a map from an external source, wherein the map identifies and controls the location of regions 426 and the various selected above described characteristics of each of regions 426. As a result, system 400 may facilitate the formation of a customized SEL stage 420 having a layout of regions and regions with selected characteristics most suited for analyzing a particular analyte or substance.

Figure 10:
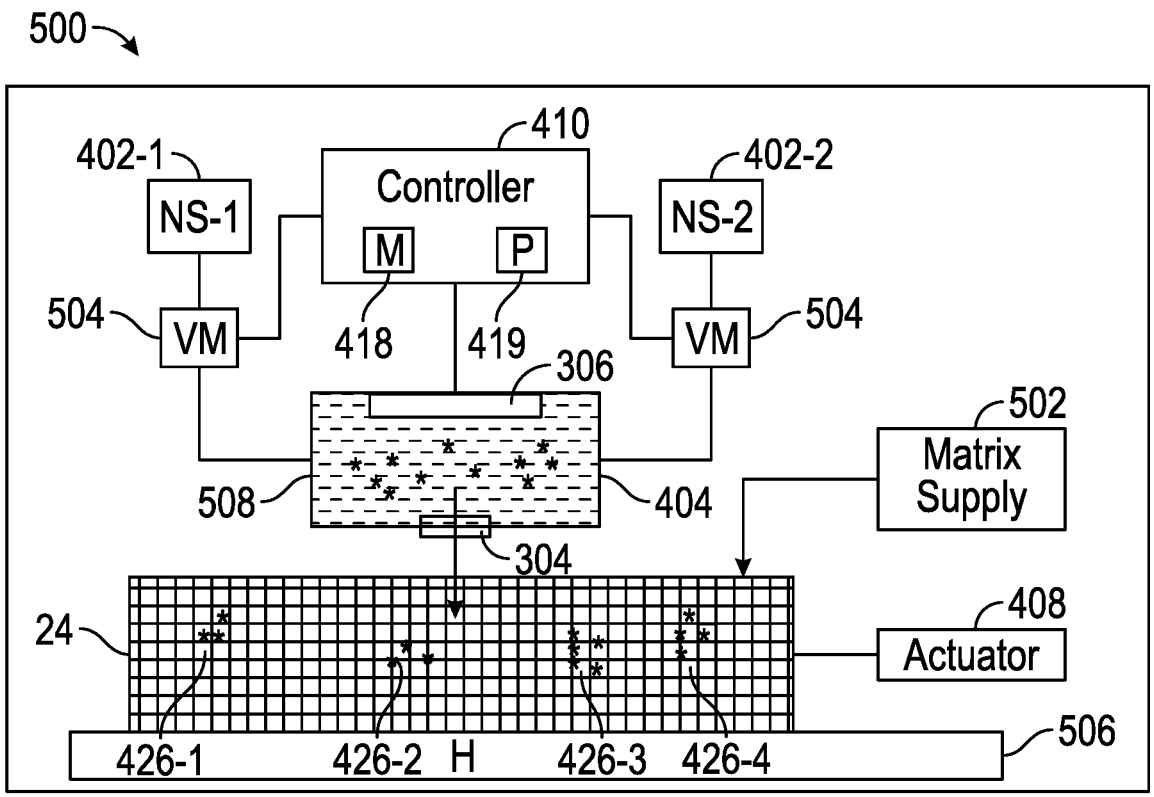
FIG. 10 is a schematic diagram of an example SEL stage forming system.

FIG. 10 schematically illustrates portions of an example SEL stage forming system 500. System 500 facilitates the formation of SEL stages having controlled populations of plasmonically active nanostructures at precise locations in different regions of the stage. In the example illustrated, system 500 for further facilitates the formation of the stage having different controlled populations of plasmonically active nanostructures at different regions of a matrix. System 500 is similar to system 400 except that system 500 is illustrated in the form of a printer. Those components of system 500 which correspond to components of system 400 are numbered similarly.

As shown by FIG. 10, in addition to comprising nano structure reservoirs 402-1 and 402-2 (collectively referred to as reservoirs 402), fluid ejector 404, actuator 408 and controller 410, system 500 is specifically illustrated as comprising matrix supply 502, valve mechanisms 504 and heater 506. In some implementations, system 500 may additionally comprise location sensor 406 and/or actuator 412 as illustrated and described above with respect to system 400.

Matrix supply 502 supplies matrix 24, wherein actuator 408 positioned matrix 24 relative to nozzle 304 of fluid ejector 404. In one implementation, matrix supply 502 comprises a tray containing a stack of matrix 24, wherein actuator 408 may comprise at least one driven roller which drives individual sheets relative to nozzle 304. In another implementation, matrix supply 502 may comprise a wound web of matrix 24, wherein actuator 408 comprises a rotary actuator that rotatably drives a reel or spindle, such as a take-up reel to move and position portions of the web opposite to nozzle 34. In some implementations, such as where matrix 24 is manually positioned opposite to fluid ejector 404 or where matrix 24 is manually provided to actuator 408, matrix supply 502 may be omitted.

Valve mechanisms 504 comprise selectively openable and closable mechanisms that open and close in response to control signals from controller 410 to control the supply of solution to jetting chamber 508 of fluid ejector 404 from either of reservoirs 402 or as a controlled mixture of solutions from reservoirs 402. As described above, in some implementations, such valve mechanisms 504 may be incorporated as part of fluid ejector 404 or as part of reservoirs 402.

Heater 506 comprises a device to apply heat to matrix 24 so as to reduce evaporation time. In one implementation, heater 506 comprises thermal resistive heaters located below the platform or other structure supporting matrix 24. In another implementation, heater 506 may comprise a thermal resistive heater other heater located downstream, wherein actuator 408 moves matrix 24 to the downstream heater, after the deposition of solution onto an into matrix 24. Heater 506 may operate at various temperatures and for different durations. Heater 506 may be under the control of controller 410. In some implementations, heater 506 may be omitted.

Figure 11:
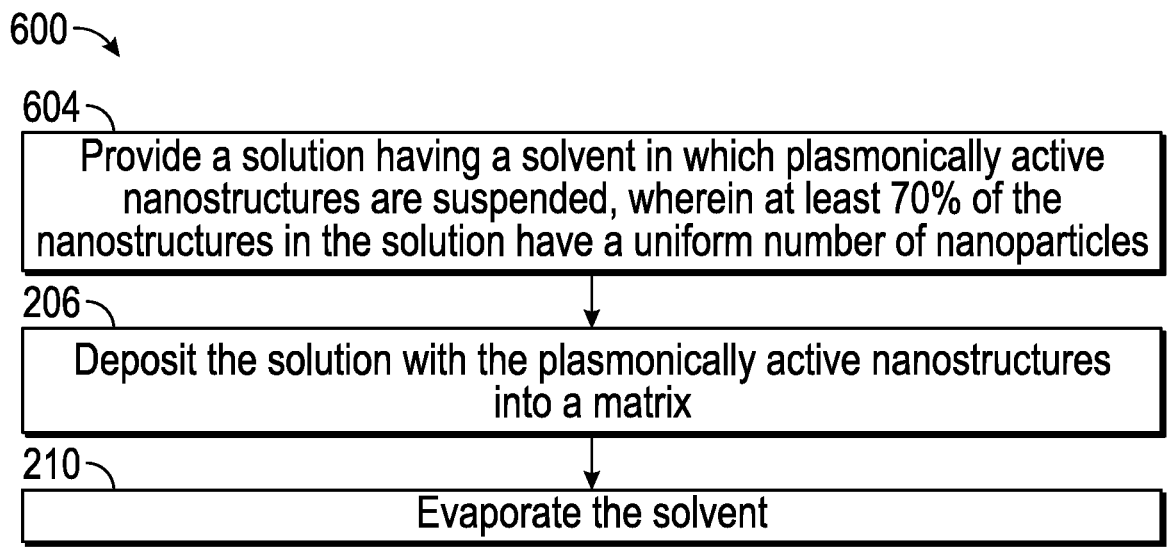
FIG. 11 is a flow diagram of an example method for forming an example SEL stage.

FIG. 11 is a flow diagram of an example method 600 for forming an example SEL stage, such as stage 24. Method 600 forms an SEL stage that provides more consistent, repeatable, reliable and accurate SEL results. Although method 600 is described in the context of forming stage 20, it should be appreciated that method 600 may likewise be utilized to form any of the described SEL stages or similar SEL stages.

Method 600 is similar to method 200 described above except that the solution that is deposited into the matrix 24 in block 206 is controlled with respect to a different aspect. As indicated by block 604, the solution is controlled such that at least 70% of the plasmonically active nanostructures in the solution have a uniform number of nanoparticles. Said another way, at least 70% of the plasmonically active nanostructures in the solution have the same number of nanoparticles. The solution with the controlled population of plasmonically active nanostructures is deposited into the matrix per block 206 and the solvent of the solution is evaporated per block 210 as described above respect to method 200.

Figure 12:
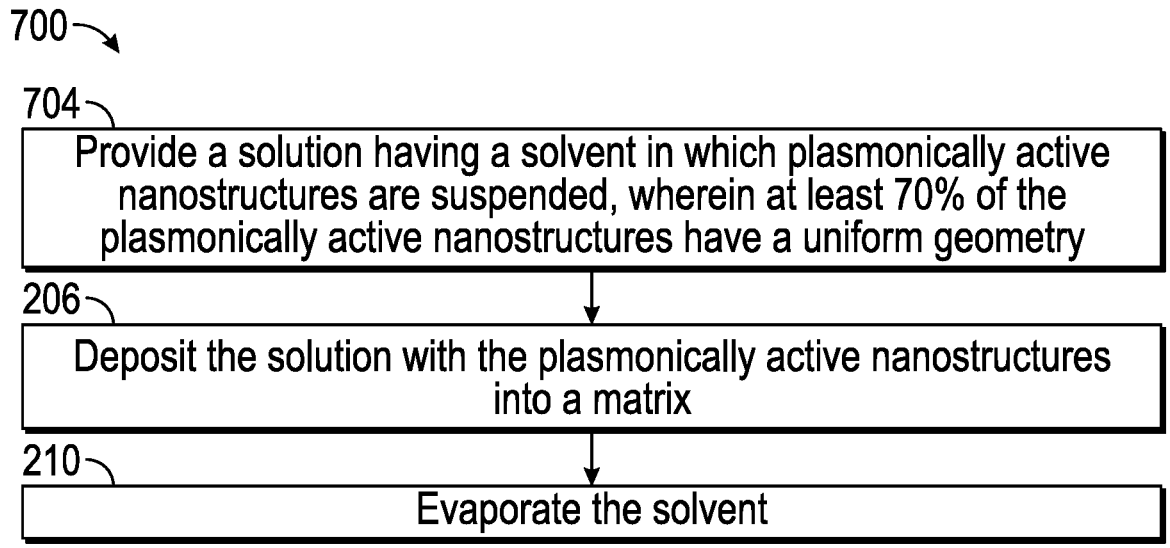
FIG. 12 is a flow diagram of an example method forming an example SEL stage.

FIG. 12 is a flow diagram of an example method 700 for forming an example SEL stage, such as stage 24. Method 700 forms an SEL stage that provides more consistent, repeatable, reliable and accurate SEL results. Although method 700 is described in the context of forming stage 20, it should be appreciated that method 700 may likewise be utilized to form any of the described SEL stages or similar SEL stages.

Method 700 is similar to method 200 described above except that the solution that is deposited into the matrix 24 in block 206 is controlled with respect to a different aspect. As indicated by block 604, the solution is controlled such that at least 70% of the plasmonically active nanostructures in the solution have a uniform geometry. Said another way, at least 70% of the plasmonically active nanostructures in the solution have the same overall shape, for example a triangular-shape such as with nano structure 130-3 in FIG. 5 or a pentagonal shape such as shown above with respect to nano structure 130-5 in FIG. 6. The solution with the controlled population of plasmonically active nanostructures is deposited into the matrix per block 206 and the solvent of the solution is evaporated per block 210 as described above respect to method 200.

Figure 13:
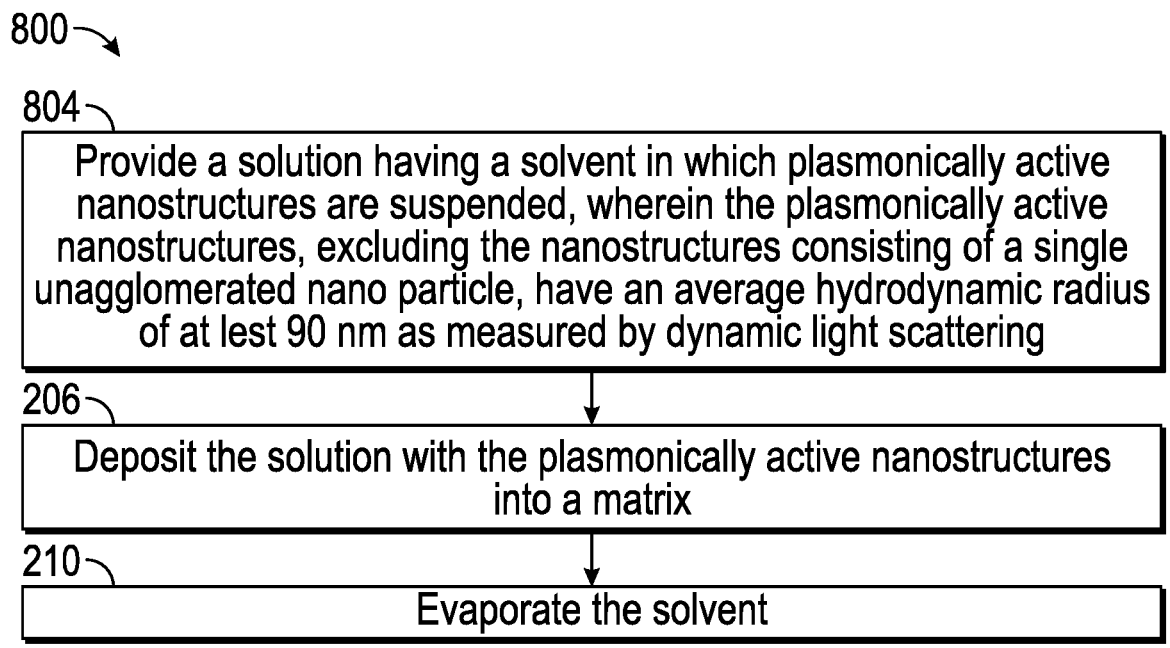
FIG. 13 is a flow diagram of an example method for forming an example SEL stage.

FIG. 13 is a flow diagram of an example method 800 for forming an example SEL stage, such as stage 24. Method 800 forms an SEL stage that provides more consistent, repeatable, reliable and accurate SEL results. Although method 600 is described in the context of forming stage 20, it should be appreciated that method 800 may likewise be utilized to form any of the described SEL stages or similar SEL stages.

Method 800 is similar to method 200 described above except that the solution that is deposited into the matrix 24 in block 206 is controlled with respect to a different aspect. As indicated by block 804, the solution is controlled such that the plasmonically active nanostructures, excluding the nanostructures consisting of a single unagglomerated nano particle, have an average hydrodynamic radius of at least 90 nm as measured by dynamic light scattering. The solution with the controlled population of plasmonically active nanostructures is deposited into the matrix per block 206 and the solvent of the solution is evaporated per block 210 as described above respect to method 200.

Figure 14:
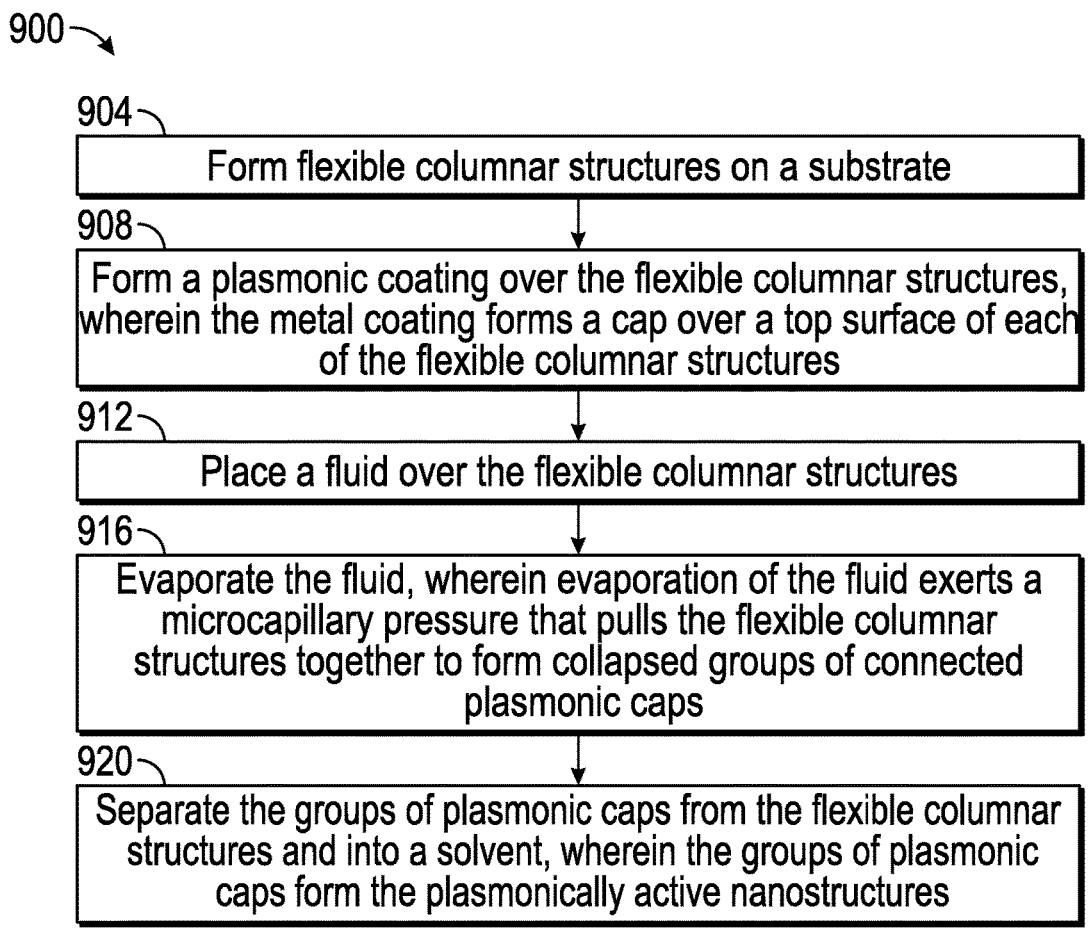
FIG. 14 is a flow diagram of an example method for forming a solution having a controlled population of plasmonically active nanostructures.

FIG. 14 is a flow diagram illustrating an example method 900 for forming a solution, such as solution 308 or the solutions provided in either of reservoirs 402, wherein the solution has a controlled population of plasmonically active nanostructures. As indicated by block 904, flexible columnar structures, such as pillars, are formed on a substrate. As indicated by block 908, a coating of a plasmonic material, such as a metal, is coated upon or over the flexible columnar structures so as to form a cap over a top surface of each of the columnar structures. In one implementation, gold or silver caps are formed on each of the columnar structures.

As indicated by block 912, a fluid is placed over the flexible columnar structures. As indicated by block 916, the fluid is subsequently evaporated. Such evaporation of the fluid exerts microcapillary pressures to pull the flexible columnar structures together to form collapsed groups of connected plasmonic caps. In some implementations, the fluid may contain emissive nano particles that attach or react with a target such that form stage may be utilized for spectroscopic tagging. For example, emissive particles that react with bacteria, proteins, DNA and the like may be provided in the solution and may be captured by the collapsed groups of connected plasmonic caps facilitate the determination of presence and concentration of a target substance using the formed stage. In other implementations, the fluid may include an analyte, a target substance itself, wherein particles or molecules of the target substance become trapped between the closed group of connected plasmonic caps. In still other implementations, the fluid may omit any such tagging particles or analyte particles.

As indicated by block 920, the groups of plasmonic caps are separated from the flexible column or structures and into a solvent. The group the plasmonic caps form the plasmonically active nanostructures. In one implementation, a sacrificial layer is formed on the columnar structures, between the college or structures and the plasmonic caps. In such an implementation, sacrificial layer is removed or otherwise treated to facilitate the separation of the groups of joined plasmonic caps from the supporting columnar structures.

In another implementation, the collapsed groups of connected plasmonic caps are embedded or surrounded by an impressionable or liquid sacrificial layer. In one implementation, sacrificial layer may be heated to a softened or molten state. The collapsed groups of connected plasmonic caps are left in place while the sacrificial layer cools and hardens. Once the sacrificial layer is hardened, the columnar structures are removed, breaking or disconnecting such structures from the supported groups of collapsed plasmonic caps. The sacrificial layer may be subsequently dissolved or otherwise removed in a solvent, forming the plasmonically active nanostructures in the solvent.

The population of the plasmonically active nanostructures in the solvent is controlled by selectively controlling or engineering the layout, proximity and collapse of the columnar structures/pillars supporting the plasmonic caps to control the number of nanoparticles in each nano structure, the shape of the formed nano structure, the size of the formed nano structure and the concentration of different types of plasmonically active nanostructures (examples of which are shown in FIGS. 3-6). For example, the columnar structures/pillars and their supported plasmonic caps may be arranged in groups of five, wherein the collapsed of such structures in the joining of their plasmonic caps will form a pentamer, forming a nano structure 130-5 as shown in FIG. 6. The columnar structures/pillars and their supported plasmonic caps may be arranged in groups of three, wherein the collapsed of such structures in the joining of their plasmonic caps will form a trimer, forming a nano structure 130-3 as shown in FIG. 5. Likewise, other nano structures may be formed through the controlled and engineered layout of such columnar structures. Because the agglomeration of nanoparticles does not rely upon relatively random agglomeration of nanoparticles in a liquid solution using aggregating agents, the resulting solution and the resulting population of plasmonically active nanostructures is more uniform and controlled to provide more reliable, consistent and repeatable sensing results using the formed SEL stage.

FIGS. 15-19 illustrate an example method for forming a solution, such as solution 308 or the solutions provided in either of reservoirs 402, wherein the solution has a controlled population of plasmonically active nanostructures. FIGS. 15-19 illustrate an example where the solution being formed, and ultimately the formed SEL stage, have a controlled population of plasmonically active nanostructures which additionally carry a captured reporter molecule. It should be appreciated that in other implementations, the reporter molecule may be omitted.

Figure 15:
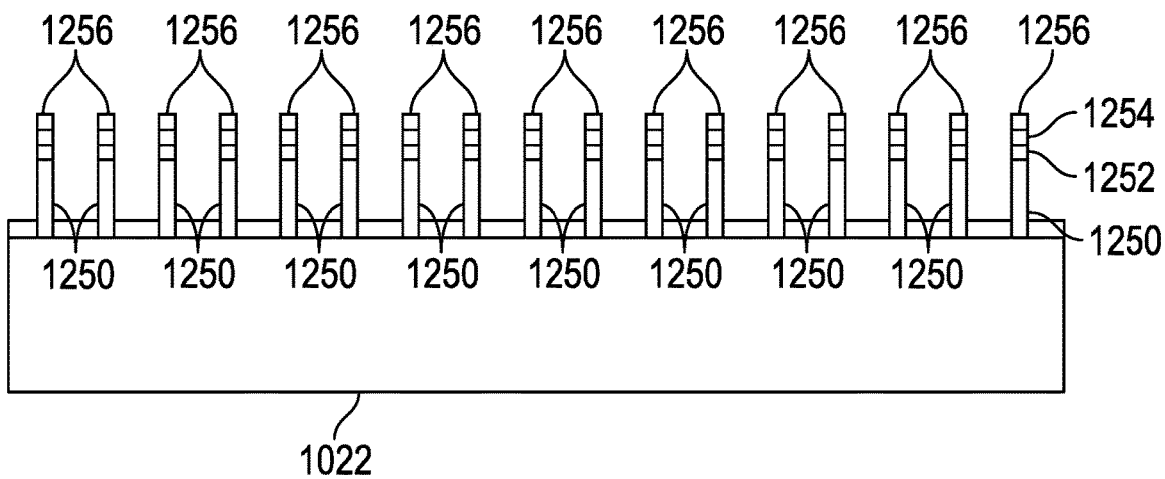
FIG. 15 is a side view schematically illustrating example posts supporting plasmonic caps for forming example plasmonically active nanostructures.

As shown by FIG. 15, flexible columnar structures, in the form of posts 1250 are formed on the surface of the substrate 1022. Posts 1250 may be formed by any number processes, including nano-embossing, lithography followed by reactive ion etching or chemical etching, UV or thermal curing, and the like. In a nano-embossing process, a layer of material may be softened and then run through a die to form the flexible post 1250.

In some examples, the posts 1250 may be deposited on the substrate 1022, for example, using nano-printing, ion deposition techniques, and the like. In a nano-printing process, the materials forming the flexible post 1250 may be directly deposited, or printed, on the surface of the substrate 1022. In other examples, nano-wires may be grown on the substrate through ion deposition. In growing the nano-wires to produce the flexible column, nano-wire seeds may be deposited onto the substrate 1022. In some examples, the nano-wire seeds may be silicon nano-structures, and the nano-wires may be silicon dioxide structures grown during chemical vapor deposition from silane.

Sacrificial material 1252 is formed as a layer upon pillars 1250. In one implementation, the sacrificial material 1252 may be deposited using a thin-film vacuum-apparatus to deposit the sacrificial material on post 1250. The sacrificial material may be deposited at an angle of about 30° to a surface of the substrate 1022 to enhance formation of the sacrificial material 1252, while decreasing the amount of sacrificial material deposited in other locations.

In other implementations, the sacrificial material 1252 may be deposited as a layer upon a layer that is to form post 1250. Thereafter, selective material removal or material forming techniques are applied to both layers to form post 1250 with the overlying sacrificial material 1252. For example, nano-embossing, lithography followed by reactive ion etching or chemical etching, UV or thermal curing, and the like may be applied to the layers.

Once the flexible posts 1250 and the overlying sacrificial material 1252 are formed, plasmonic caps 1254 may be formed over the sacrificial material 1252. The plasmonic caps 1254 may be deposited using a thin-film vacuum-apparatus to deposit metal onto the sacrificial material 1252. The plasmonic material, such as a metal, for instance gold or silver, may be deposited at an angle of about 30° to a surface of the substrate 1022 to enhance formation of the plasmonic caps 1254, while decreasing the amount of plasmonic material deposited in other locations. The material deposited from the plasmonic vapor (such as metal vapor) may also be limited to control the deposition, and lower the amount deposited on the substrate 1022 or on sides of the post 1250.

Other techniques may be used to form the plasmonic caps 1254. In some examples, the substrate 1022 including the flexible post 1250 and sacrificial material 1252 may be immersed in a plating solution that includes metal cations. An electric potential applied to the substrate 1022 may cause deposition of metal at the top of the sacrificial material 1252, as the top of the sacrificial material 1252 may have a more concentrated or enhanced electrical field. The plasmonic caps 1254 may be precipitated from colloidal suspensions of metallic nanoparticles when an electric potential is applied to the substrate 1022. Any number of other techniques may be used to form the plasmonic caps 1254.

Thereafter, cover layer 1256 is formed upon metallic caps 1254. Cover layer 1256 may be formed upon metallic caps 1254 in the same manner as sacrificial material 1252 was formed upon post 1250. In one implementation, cover layer 1256 may be deposited using a thin-film vacuum-apparatus to deposit the cover layer 1256. The cover layer 1256 may be deposited at an angle of about 30° to a surface of the substrate 1022 to enhance formation of the cover layer 1256, while decreasing the amount of the material of cover layer 1256 deposited in other locations.

Figure 16:
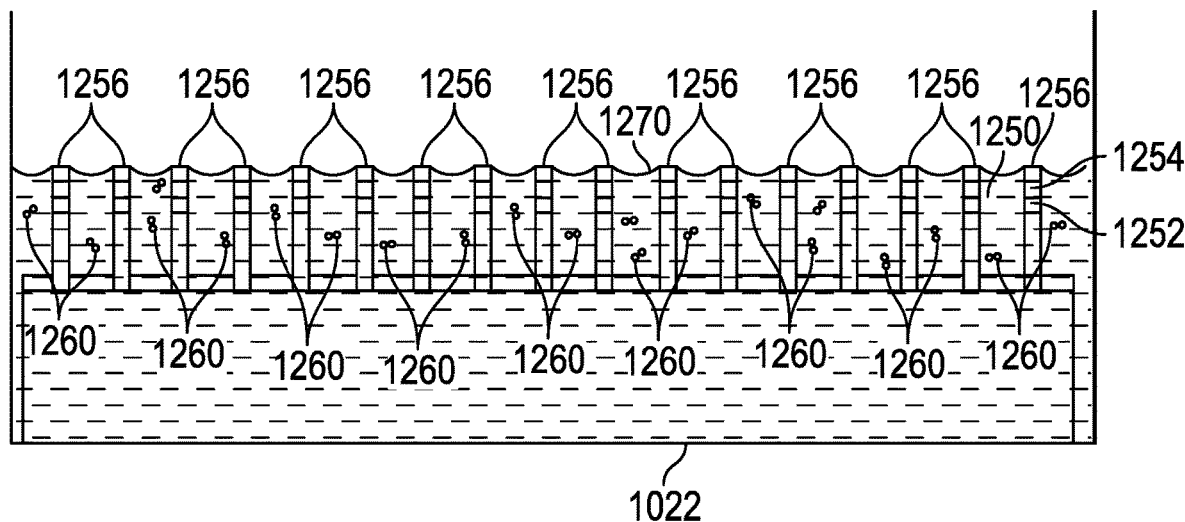
FIG. 16 is a side view schematically illustrating the example posts immersed in an example fluid containing reporter molecules.
Figure 17:
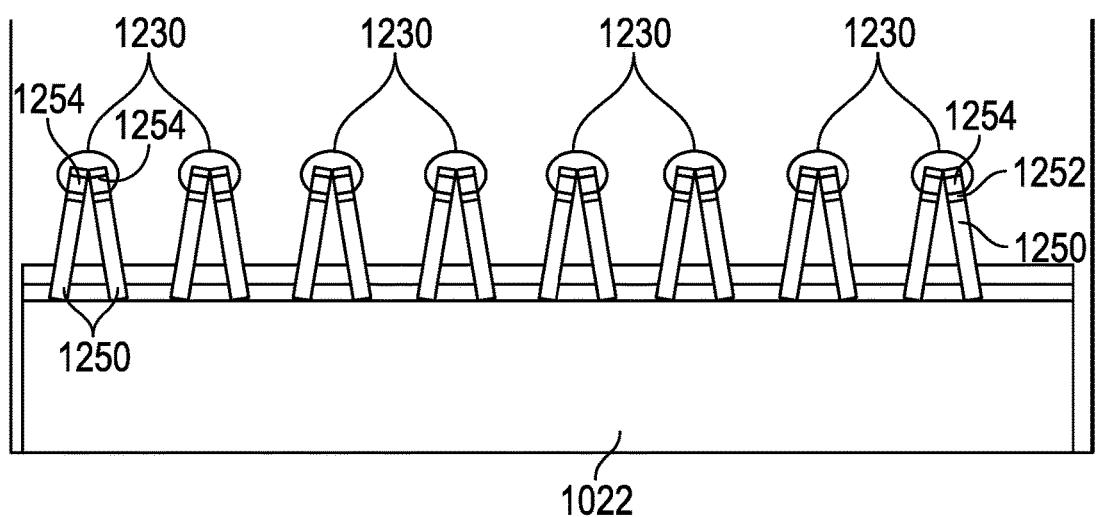
FIG. 17 is a side view schematically illustrating evaporation of the fluid and an example closure of the posts to capture the reporter molecules and form anchored plasmonically active nanostructures.

FIGS. 16 and 17 illustrate the absorption of the reporter molecule 1260 on the metallic caps 1254. As shown by FIG. 16, the nano pillars are submersed in a fluid 1270 containing the reporter molecules 1260. As shown by FIG. 17, the fluid 1270 is subsequently evaporated. Evaporation of the fluid 1270 provides increased microcapillary pressure around the post 1250. This causes flexible post 1250 to collapse, bringing the plasmonic caps 1254 of adjacent post 1250 together, forming a cluster of plasmonic nano-particles attached to the flexible posts 1250. In some examples, the fluid 1270 with the reporter molecules 1260 may be incubated before the evaporation to allow reactions before the evaporation.

Multiple fluids may be used in the preparation. For example, the reporter molecules 1260 may be dissolved in a first fluid and the flexible posts 1250 and plasmonic caps 1254 may be incubated to allow reaction. A clean fluid may be used to rinse the surface to eliminate excess reporter molecules 1260. The same fluid or another fluid may then be evaporated from the surface to collapse the post 1250. Reporter molecules 1260 do not have to be added by dissolution in the fluid 1270. In some examples, the plasmonic caps 1254 of the flexible posts 1250 may be reacted with gas phase reporter molecules after which a fluid 1270 may be used to collapse the flexible posts 1250.

FIG. 17 illustrates an example of collapsed groups 272 formed by the evaporation of the fluid 1270. The reporter molecules 1260 may be adsorbed on the surfaces of the plasmonic caps 1254, or may be trapped in the nm-scale gaps between the plasmonic caps 1254. The number of plasmonic caps 1254 in each collapsed group of posts 1250 may vary depending on the dynamics of the collapse process. For example, a collapsed group 1254 may include a cluster of metallic nano-particles formed from two plasmonic caps 1254, three plasmonic caps 1254, four plasmonic caps 1254, or five plasmonic caps 1254, or more. The pentamer shape, formed from five plasmonic caps 1254, has been shown to have particularly good performance on a substrate and may also perform well in solution due to the large number of dipole axes.

Figure 18:
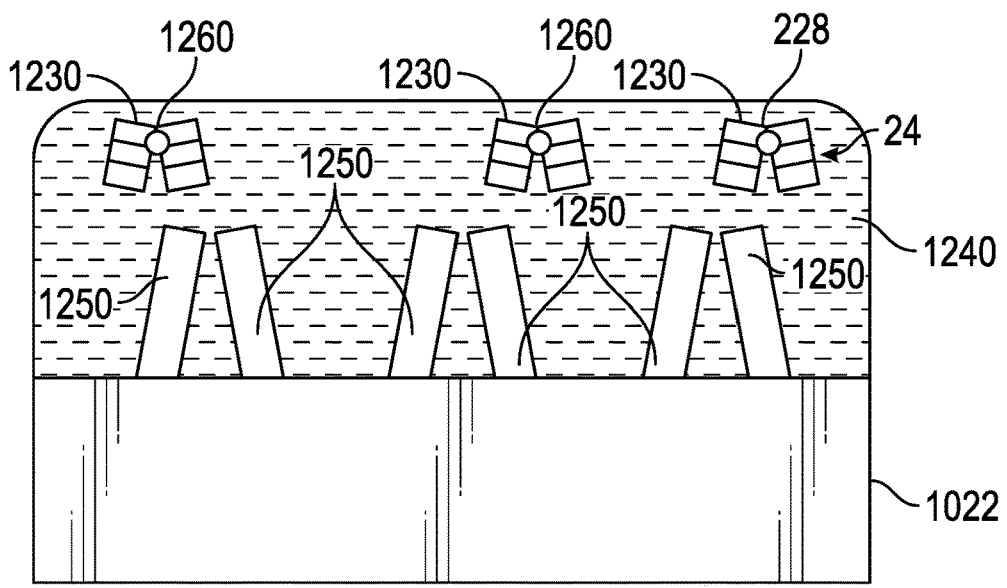
FIG. 18 is a sectional view illustrating example disanchoring of the example plasmonically active nanostructures in a solvent.

FIG. 18 illustrates the release of or dis-anchoring of the individual plasmonically active nanostructures 1230. As shown by FIG. 18, while being exposed to solvent 1240, plasmonically active nanostructures 1230, formed by joined plasmonic caps 1254 are released and become suspended within solvent 1240. In one implementation, sacrificial material 1252 is formed from a material that dissolves in solvent 1240, wherein plasmonically active nanostructures 1230 become suspended in the solvent 1240. In one implementation, sacrificial material 1252 may comprise aluminum. In another implementation, sacrificial material 1252 may comprise PMMA which dissolves in a solvent 1240, such as acetone.

Figure 19:
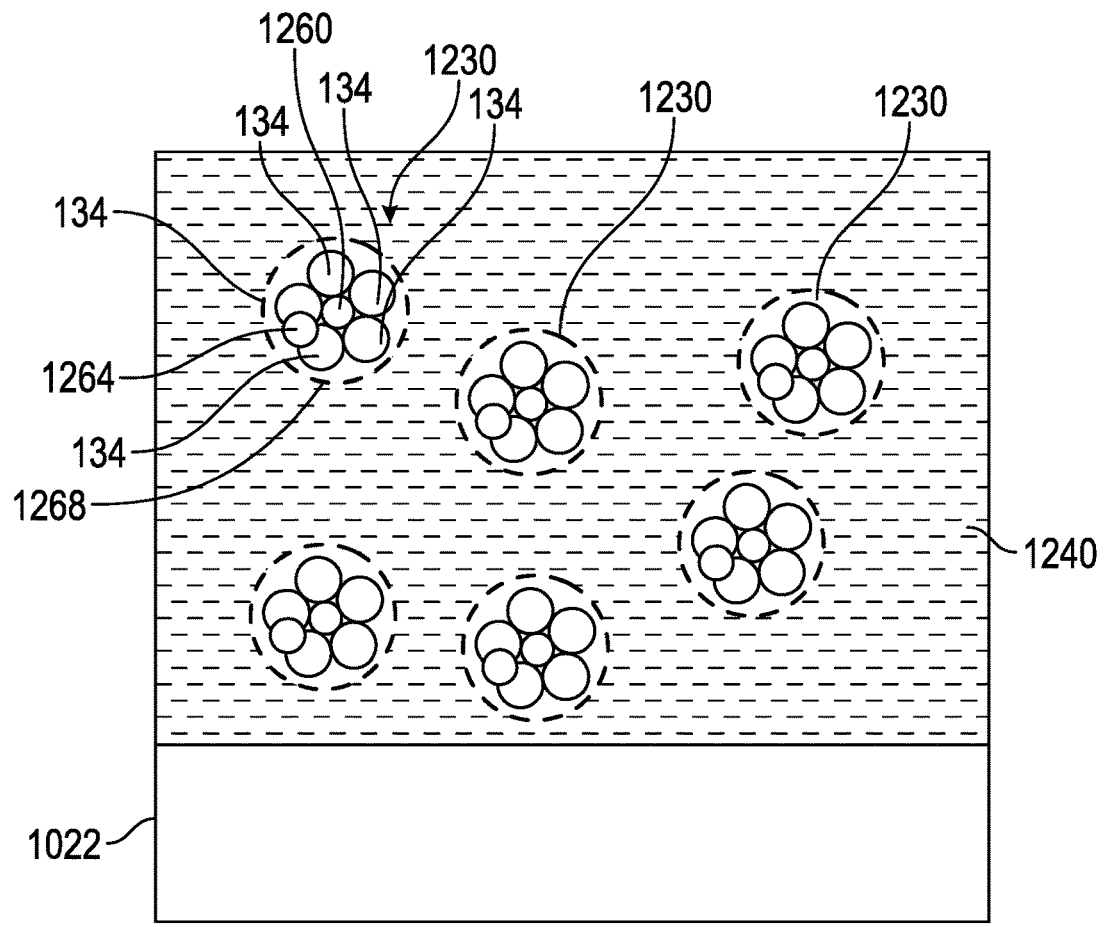
FIG. 19 is a sectional view illustrating the example plasmonically active nanostructures suspended in the solvent.

FIG. 19 illustrates the separated plasmonically active nanostructures 1230 suspended or otherwise supported in solvent 1240. Each nano structure 1230 comprises a cluster or grouping of individual nanoparticles 134 providing plasmonically active surfaces. The plasmonic active surfaces may comprise a metal. For example, the plasmonically active surfaces of the individual particles may comprise noble metals, such as ruthenium (Ru), rhodium (Rh), palladium (Pd), silver (Ag), osmium (Os), iridium (Ir), platinum (Pt), and gold (Au), as well as copper, or alloys thereof. Other metals may be used provide the plasmonic surfaces, such as aluminum (Al), titanium (Ti), or other metals.

Although each nano structure 1230 is illustrated as comprising five adjacent nanoparticles 134, in other implementations, each nano structure 1230 may comprise other numbers of nanoparticles assembled or held adjacent to one another. For example, each nano structure 1230 may comprise a dimer, trimer or tetramer. Junctions between the nanoparticles of the nano structure 1230 form at least one "hot spot".

In the example illustrated, each nano structure 1230 further comprises at least one reporter molecule 1260 (sometimes referred to as a spectroscopic tagging molecule) may be captured or trapped in the junctions, wherein the reporter molecule 1260 emits a signature radiation pattern, which is enhanced as a result of the molecule being captured in the hotspot. The reporter molecules 1260 may be any number of molecules that give a spectroscopic response, for example, in a surface enhanced luminescence technique. For use in SERS, the reporter molecule may be trans-1, 2-bis (4-pyridyl) ethylene. However, any number of other reporter molecules 360 may be used depending on the spectroscopic techniques.

In the example illustrated, each nano structure 1230 is additionally functionalized using functionalizing molecules 1264 with the binding agent on one end and a functional group on the other end. For example, the binding agent may include thiols for binding to the exposed portion of the plasmonic surface of the nano structure 1230. In one implementation, the functionalizing molecules 1264 are adhered to nano structure 1230 after nano structure 1230 have been dis-anchored and are suspended in solvent 1240. In other implementations, the functionalizing module 1264 are provided as part of each nano structure 1230 prior to the nano structure 1230 being dis-anchored.

The functional group may be designed to promote stability in solution, bind to specific substrates or tissues, or both. Multiple functionalization molecules can also be utilized. One example of a functional group may be a monoclonal antibody selected to bind to an express group on the surface of a cell. The functional group may comprise a short DNA segment that is to bind to a complementary DNA segment. A functional group may comprise a long paraffinic chain that stabilizes the nano structure 1230 in organic materials, such as solvents, fatty acids, triglycerides and the like.

In some implementations, the functional group may be a therapeutic agent. For example, therapeutic agent may be released when the nano structure 1230 is exposed to an excitation source. In such an implementation, the functional group may facilitate the delivery of local therapeutics with a plasmonically activated drug delivery system using nano structure 1230.

In some implementations, nano structure 1230 may be tuned to specific applications. For example, in some implementations, the size and/or geometry of nano structure 1230 may be customized for a particular application such as where the nano structure 1230 is intended to bind to a particular substrate or tissue, where the nano structure 1230 is to pass through cell walls or where the nano structure 1230 is to be utilized in solution.

In some implementations, the nano structure 1230 may be encapsulated or covered with a protective outer coating 1268 (shown by broken lines) that may protect any reporter molecules or stabilize the nano structure 1230 in solution. For example, the protective coating may promote stability of a suspension or block further aggregation of the nano particle structure 1230. Examples of such a coating include, but are not limited to, silicon dioxide, metal oxides, metal carbides, metal sulfide, diamond, spinel structures ($MgAl_2O_4$) and the like. Protective coating may be applied using a vapor deposition technique, atomic layer deposition or liquid deposition techniques.

Figure 20:
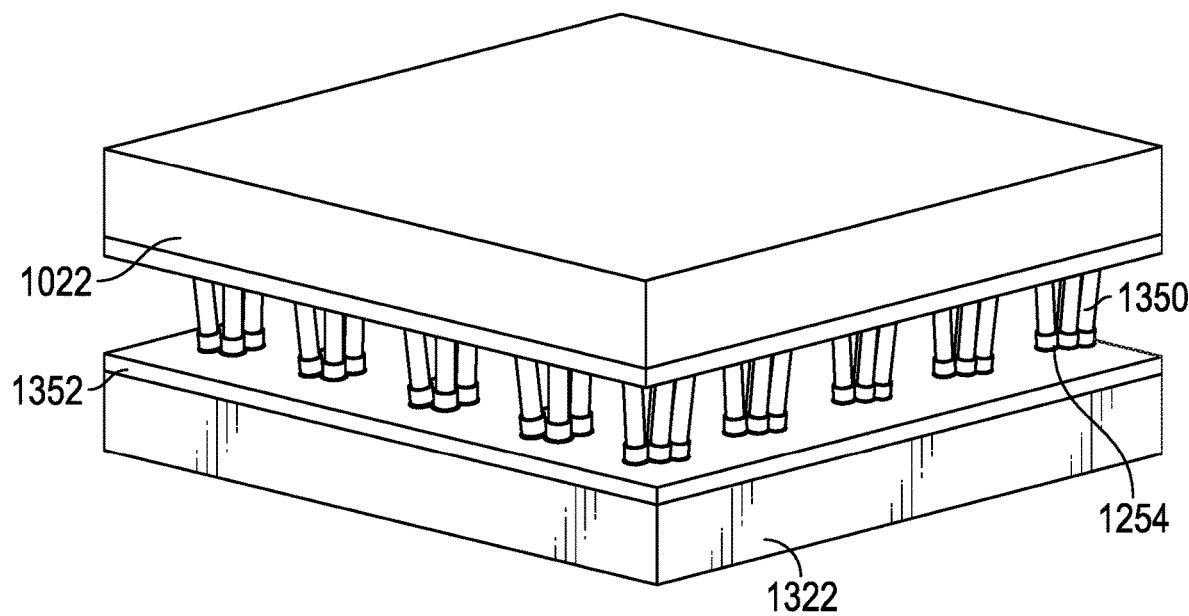
FIG. 20 is a perspective view illustrating an example of the embedding of plasmonic caps and reporter molecules of closed posts into a sacrificial layer.
Figure 21:
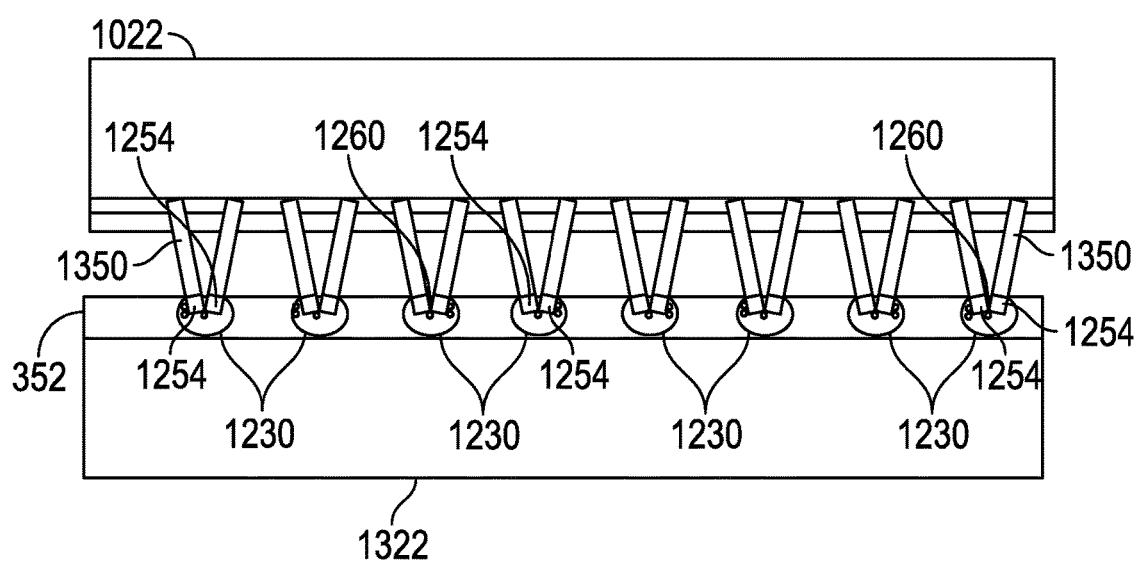
FIG. 21 is a sectional view illustrating an example of the embedding of the plasmonic caps and reporter molecules of the closed posts into the sacrificial layer.
Figure 22:
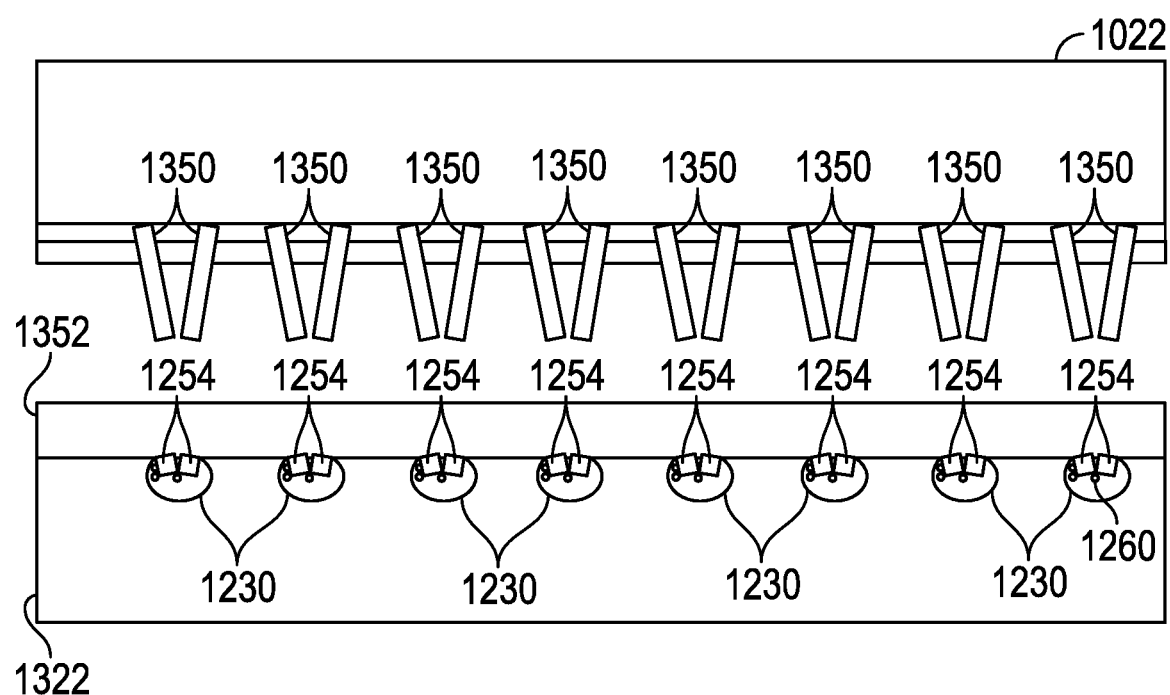
FIG. 22 is a sectional view illustrating an example of separation of posts, from the plasmonic caps, leaving the example plasmonically active nanostructures embedded in the sacrificial layer.

FIGS. 20-22 illustrate an example method for forming a solution, such as solution 308 or the solutions provided in either of reservoirs 402, wherein the solution has a controlled population of plasmonically active nanostructures. FIGS. 20-22 illustrate an example where the solution being formed, and ultimately the formed SEL stage, have a controlled population of plasmonically active nanostructures which additionally carry a captured reporter molecule. It should be appreciated that in other implementations, the reporter molecule may be omitted.

As shown and discussed above with respect to FIGS. 15 and 16, post 1350 are formed on a platform 1022. Posts 1350 are similar to posts 1250 described above and are formed in a similar fashion except the posts 1350, in some implementations, may omit sacrificial layer 1252 and sacrificial layer 1254, wherein plasmonic caps 1254 are formed directly upon posts 1350. The posts 1350 may be closed and the reporter molecules 1260 may be adhered to the closed posts 1350 as described above with respect to FIG. 17.

As further shown by FIGS. 20 and 21, platform 1022 and the closed posts 1350, along with the captured reporter molecules 1260, are inverted opposite to substrate 1322 and its overlying layer 1352 of sacrificial material. The collapsed groups of posts 1350 are pressed into the sacrificial layer 1352, which is fluid. For example, in one implementation, sacrificial layer 1352 may be heated to a softened or molten state. The collapsed groups of posts 1350 are left in place while the sacrificial layer 1352 cools and hardens.

As shown by FIG. 22, once the sacrificial layer 1352 has hardened, the platform 1022 and the retained posts 1350 may be removed. The removal of the platform 1022 may break or disconnect the posts 1350 from the plasmonic caps 1254, leaving the closed group of plasmonic caps 1254, forming plasmonically active nanostructures 1230 and the adhered reporter molecules 1260 embedded in the sacrificial layer 1352. As shown by FIG. 19, sacrificial layer 1352 may be subsequently removed, such as by being dissolved in a solvent 1240, to suspend the thus formed plasmonically active nanostructures 1230 in the solvent 1240.

Although the present disclosure has been described with reference to example implementations, workers skilled in the art will recognize that changes may be made in form and detail without departing from the scope of the claimed subject matter. For example, although different example implementations may have been described as including features providing benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A surface enhanced luminescence (SEL) sensing stage comprising:
   a matrix;
   plasmonically active nanostructures retained within the matrix, wherein no greater than 10% of the plasmonically active nanostructures consist of a single unagglomerated plasmonically active nano particle.

2. The SEL sensing stage of claim 1, wherein no greater than 5% of the plasmonically active nanostructures consist of a single unagglomerated plasmonically active nano particle.

3. The SEL sensing stage of claim 1, wherein at least 70% of the plasmonically active nanostructures have a uniform number of nanoparticles.

4. The SEL sensing stage of claim 1, wherein at least 90% of the plasmonically active nanostructures have a uniform number of nanoparticles.

5. The SEL sensing stage of claim 1, wherein at least 70% of the plasmonically active nanostructures have a uniform geometry.

6. The SEL sensing stage of claim 5, wherein the uniform geometry comprises a pentamer of five plasmonically active nanoparticles.

7. The SEL sensing stage of claim 1, wherein at least 90% of the plasmonically active nanostructures have a uniform geometry.

8. The SEL sensing stage of claim 1, wherein the plasmonically active nanostructures, excluding the nanostructures consisting of a single unagglomerated nano particle, have an average hydrodynamic radius of at least 90 nm as measured by dynamic light scattering.

9. The SEL sensing stage of claim 1, wherein the matrix omits an aggregating agent.

10. The SEL sensing stage of claim 1 further comprising a residue from an evaporated solvent selected from a group of solvents consisting of: acetone, ethanol, alcohol dimethyl sulfoxide and water.

11. The SEL sensing stage of claim 1 further comprising second plasmonically active nanostructures retained within the matrix, the plasmonically active nanostructures having a first constitution and located within a first predefined and controlled region of the matrix and the second plasmonically active nanostructures having a second constitution different than the first constitution, the second plasmonically active nanostructures being located within a second predefined and controlled region of the matrix.

12. The SEL sensing stage of claim 1 further comprising second plasmonically active nanostructures retained within the matrix, wherein the plasmonically active nanostructures have a first average size and are located within a first predefined and controlled region of the matrix and wherein the second plasmonically active nanostructures having a second average size different than the first average size, the second plasmonically active nanostructures being located within a second predefined and controlled region of the matrix.

13. The SEL sensing stage of claim 1, wherein the matrix comprises a matrix selected a from a group of matrices consisting of: a nitrocellulose membrane polymer having an electrostatic binding mechanism, a polyvinylidene fluoride membrane polymer having a hydrophobic primary binding mechanism, a (discharge-modified) nylon membrane polymer having an (ionic) electrostatic primary binding mechanism and a polyestersulfone membrane polymer having a hydrophobic primary binding mechanism.

14. The SEL sensing stage of claim 1, wherein the plasmonically active nanostructures each comprise a spectroscopic tagging molecule.

15. The SEL sensing stage of claim 1, wherein the matrix comprises internal voids partially filled with the plasmonically active nanostructures.

16. A method comprising:
providing a solution having a solvent in which plasmonically active nanostructures are suspended, wherein at least 70% of the nanostructures in the solution have a uniform number of nanoparticles;
depositing the solution with the plasmonically active nanostructures into a matrix; and
evaporating the solvent.

17. The method of claim 16, wherein the depositing of the solution with the plasmonically nanostructures into the matrix comprises controllably jetting the solution in at least one predefined location of the matrix.

18. The method of claim 17, wherein the controllable jetting of the solution comprises heating the solution to a temperature above a nucleation temperature of the solution to create a bubble which expels surrounding portions of the solution through a nozzle.

19. The method of claim 16, wherein the providing of the solution having the solvent in which the plasmonically nanostructures are suspended comprises:
forming flexible columnar structures on a substrate;
forming a metal coating over the flexible columnar structures, wherein the metal coating forms a cap over a top surface of each of the flexible columnar structures;
placing a fluid over the flexible columnar structures;
evaporating the fluid, wherein evaporation of the fluid exerts a microcapillary pressure that pulls the flexible columnar structures together to form collapsed groups of connected metallic caps; and
separating the groups of metallic caps from the flexible columnar structures and into the solvent, wherein the groups of metallic caps form the plasmonically active nanostructures.

20. A surface enhanced luminescence (SEL) applicator comprising:
a first reservoir containing a first solution of a solvent in which plasmonically active nanostructures are suspended, wherein no greater than 10% of the plasmonically active nanostructures consist of a single unagglomerated plasmonically active nano particle;
a nozzle;
a fluid actuator to controllably eject the first solution through the nozzle into a matrix;
a second reservoir containing a second solution of a second solvent in which second plasmonically active nanostructures are suspended, wherein the plasmonically active nanostructures have a first constitution and wherein the second plasmonically active nanostructures have a second constitution different than the first constitution;
a first valve mechanism to controllably supply the first solution from the reservoir to the fluid actuator; and
a second valve mechanism to controllably supply the second solution from the second reservoir to the fluid actuator.

* * * * *